United States Patent [19]

Smith et al.

[11] Patent Number: 5,465,605
[45] Date of Patent: Nov. 14, 1995

[54] FLOOR COVERING FOOT IMPACT SIMULATOR

[76] Inventors: Gary W. H. Smith; Garrick D. S. Smith, both of 7678 State Hwy. 89, Columbus, Wis. 53925

[21] Appl. No.: 93,865

[22] Filed: Jul. 19, 1993

[51] Int. Cl.⁶ ................................................ G01N 3/56
[52] U.S. Cl. ................ 73/7; 73/838; 73/865.6; 73/866
[58] Field of Search .................... 73/838, 7, 10, 73/840, 865.6, 866

[56] References Cited

U.S. PATENT DOCUMENTS

| | | | |
|---|---|---|---|
| 2,251,681 | 8/1941 | Hathaway et al. | 73/51 |
| 2,895,326 | 7/1959 | Fesperman et al. | 73/7 |
| 3,102,414 | 9/1963 | Wharff, Jr. | 73/7 |
| 3,286,505 | 11/1966 | Penman et al. | 73/7 |
| 3,323,349 | 6/1967 | Savage et al. | 73/7 |
| 3,364,726 | 1/1968 | Bonham | 73/7 |
| 3,382,701 | 5/1968 | Powell | 73/7 |
| 3,427,859 | 2/1969 | Taub | 73/7 |
| 3,516,281 | 6/1970 | Taub | 73/7 |
| 3,641,807 | 2/1972 | Brooks | 73/7 |
| 3,681,969 | 8/1972 | McCord | 73/7 |
| 3,835,697 | 9/1974 | Schneider et al. | 73/7 |
| 3,971,245 | 7/1976 | Crafford et al. | 73/7 |
| 4,096,733 | 6/1978 | Cohen | 73/7 |
| 4,130,007 | 12/1978 | Hayashi | 73/7 |
| 4,936,135 | 6/1990 | Annis et al. | 73/7 |

*Primary Examiner*—Richard Chilcot
*Assistant Examiner*—George M. Dombruske
*Attorney, Agent, or Firm*—Reinhart, Boerner, Van Deuren, Norris & Rieselbach

[57] ABSTRACT

A reciprocating pneumatic cylinder is mounted to drive a simulated heel at an angle of 15 to 20 degrees into a floor covering system which is mounted to move back and forth and rotate with respect to the heel impacts. The impacts are thereby varied in angle of attack over the surface of a test specimen and are simulative of human foot traffic. A carpet sample is stretched beneath the impacting heel over a cushion 56 which is unstretched. A bidirectional clamping assembly allows readings to be taken during a test to determine dimensional stability and rate of change of dimensional stability. The test specimen which results from multiple impacts has a central region which is heavily worked and an outer region which is subjected to fewer impacts, permitting a range or wear to be analyzed on a single specimen. Carpet response to soiling may also be examined on a test specimen.

14 Claims, 7 Drawing Sheets

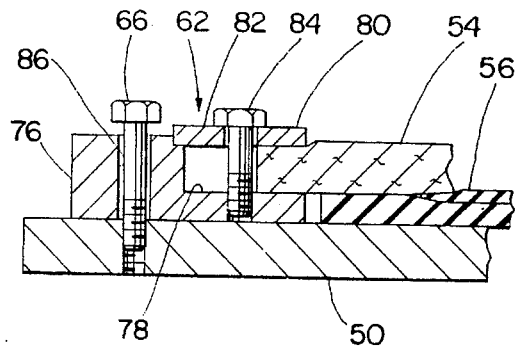
Fig. 3
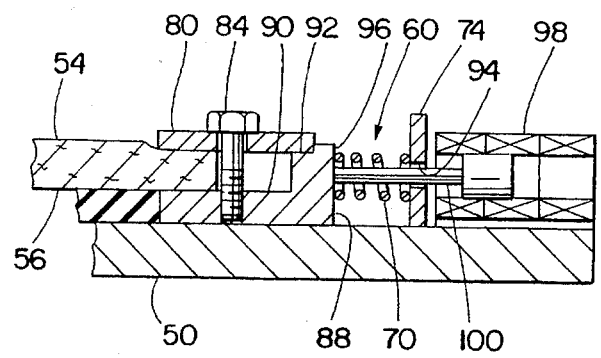
Fig. 4
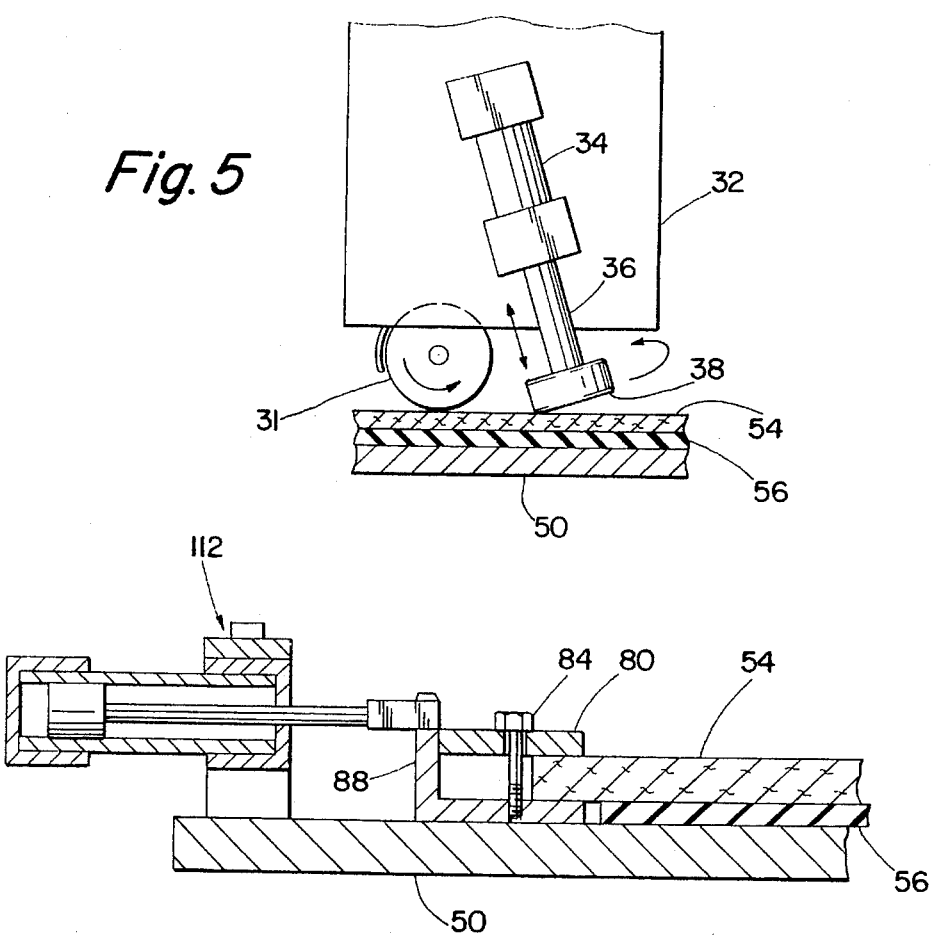
Fig. 5
Fig. 6

FLOOR COVERING FOOT IMPACT SIMULATOR

FIELD OF THE INVENTION

This invention relates to material wear testers and methods in general and to apparatus and methods for testing carpets and floor coverings in particular.

BACKGROUND OF THE INVENTION

Carpet wear testing is a particularly important facet of the carpet industry. Carpets are normally expected to last 20 or more years and are often sold with warranty periods of five or ten years. Thus, it is readily apparent that the industry can ill-afford to wait five, ten or even twenty years before determining the wear and durability capabilities of a particular carpet. Carpet wear testers have been developed which utilize a pneumatic impactor to repetitively impinge upon a carpet sample. The carpet sample is normally clamped to a test table and moved relative to the pneumatic impactor, thus causing the location of the impacts on the carpet to traverse the carpet sample in a repeated pattern. The clamps in known carpet testers have employed springs for keeping the carpet sample under constant or nearly constant tension while it is impacted by a simulated shoe or other wear producing device. Known carpet wear testers have employed cams and mechanical linkages to produce repeated traverse patterns over the carpet test samples but have in general been limited to one or few test patterns.

Human foot traffic, however, is extremely varied and multidirectional. A foot step involves not only the forces of a downwardly directed impact but shear on the floor covering as the foot moves forward while impacting and lifting from the surface. Prior art testing equipment has failed to properly simulate these forces or has utilized a unidirectional shear simulation.

Conventional industry tests work carpet samples as isolated units, for example by lining a rotating drum with the sample and oscillating an independent ball or weight for repeated random impacts. Such a test produces a carpet which is fully worked over its entire surface. It does not provide any range of data. Furthermore, this type of test does not take into account the support or lack thereof provided by the cushion or backing material.

While known carpet testers are effective for producing wear in carpets, they lack the flexibility to address current issues in carpet wear. Conventional carpet testers produce worn samples of carpet which may be evaluated but do not produce real time feedback of the material properties of the carpet sample being tested which may be used in real time to modify the actions of the carpet tester. Furthermore, known carpet testers do not allow computer control of the wear impactor's traversing course nor the use of an actual database of the dynamics of a person traversing a carpet to control a carpet tester.

What is needed is a floor covering testing apparatus which mimics the actual intensity and direction of forces applied under actual environmental conditions which permits analysis of the changing attributes of a floor covering system over time and which generates a tested specimen which provides a wide range of testing data.

SUMMARY OF THE INVENTION

The floor covering foot force simulator of the present invention provides a means for testing carpeting and floor coveting systems which is simulative of human foot traffic and which is generally repeatable. The floor coveting to be tested is held in place on a specimen table and moved in a reciprocating back and forth motion in a horizontal plane with respect to an angled impactor which has a simulated shoe heel for repeated impacting of the floor covering. In addition, the impactor continuously rotates with respect to the floor covering, yielding impacts from all possible angles of attack.

A floor covering system which comprises a carpet and a backing cushion is tested by clamping the carpet specimen in a bidirectional clamp above the cushion, such that the carpet is free to stretch over the cushion. Data readings are taken on the amount of carpet stretch over a period of repeated impacts to determine the dimensional stability of the carpet. Either the specimen table or the impactor may be mounted for movement while the other remains stationary.

The pattern traced by the impactor produces a specimen which is worked more intensely at its center and less so at its outer regions. Such a specimen is useful in that it allows analysis and comparison of the effects of different degrees of wear on a single test specimen It is an object of the present invention to provide a floor covering tester which records the physical properties of the carpet with respect to time or wear-producing events.

It is another object of the present invention to provide a toot force simulator which simulates both the changing shear and compression forces exerted on a floor covering by human footsteps.

It is an additional object of the present invention to provide a testing apparatus for multi-component carpet systems which simulates installation conditions.

It is also an object of the present invention to provide a carpet tester which produces a wear pattern on a test sample which is graduated from one level of wear to another.

It is a still further object of the present invention to produce a carpet wear tester suitable for use as an industry-wide standard for the comparison of one lot of carpet with another.

Further objects, features and advantages of the invention will become apparent from the following detailed description when taken in conjunction with the accompanying drawings.

BRIEF DESCRIPTION OF THE DRAWINGS

FIG. 3 is a cross-sectional view of the apparatus of FIG. 2 taken along section line 3—3.

FIG. 4 is a cross-sectional view of the apparatus of FIG. 2 taken along section line 4—4.

FIG. 5 is a detail view of the pneumatic impactor of the apparatus of FIG. 1.

FIG. 6 is a cross-sectional view of an alternative embodiment floor covering tester of the present invention taken through a controlled tensioning pneumatic cylinder.

DESCRIPTION OF THE PREFERRED EMBODIMENTS

Figure 1:
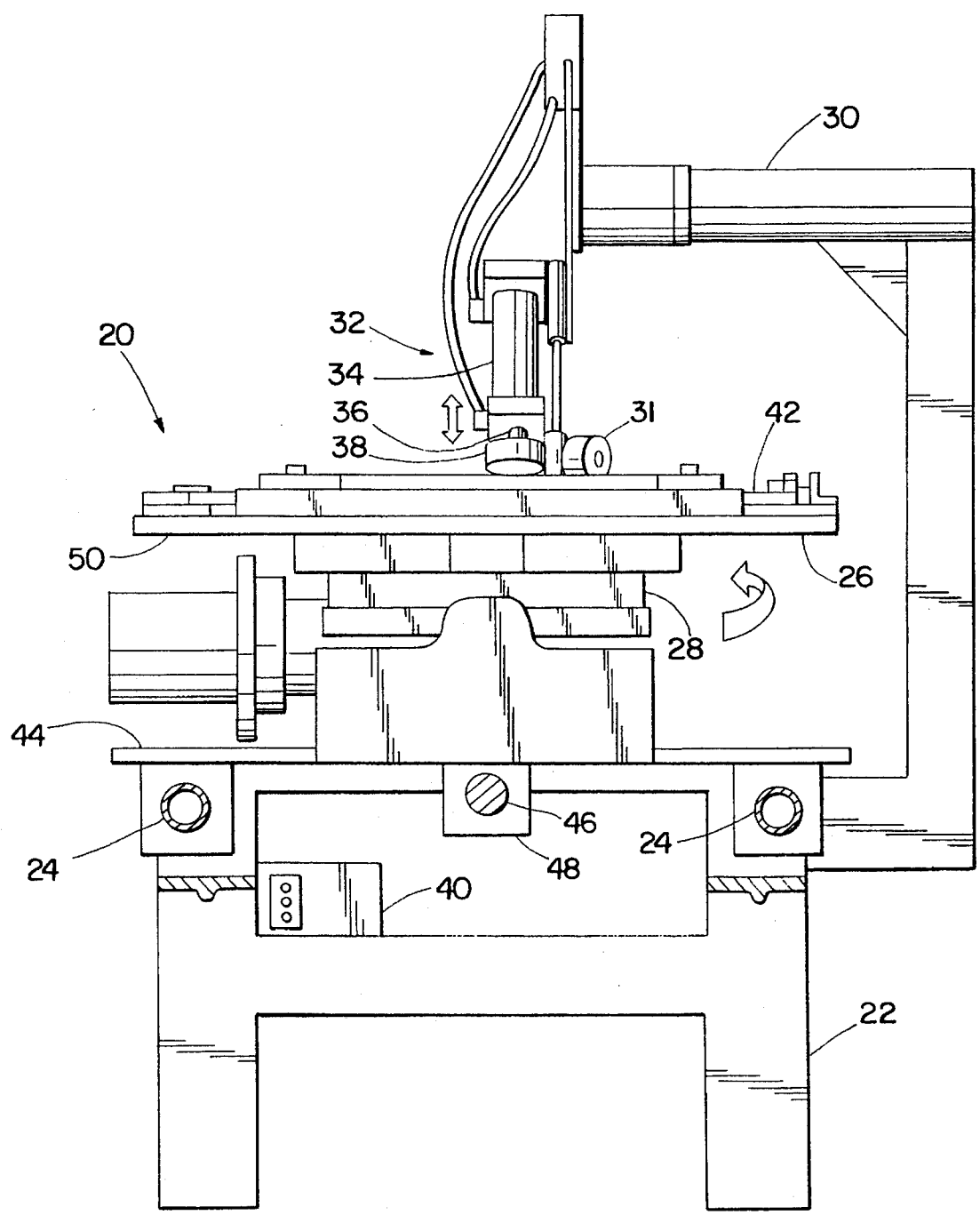
FIG. 1 is a front elevational view of the floor covering tester of this invention.

Referring more particularly to FIGS. 1–13, wherein like numbers refer to similar parts, a floor covering wear tester and foot force impact simulator 20 is shown in FIG. 1. The simulator 20 subjects floor covering systems to controlled impacts which provides an accelerated assessment of the wear characteristics of the floor covering. The dam gained from analysis of the test results may be utilizing in predicting the performance of the floor covering under real world conditions.

The simulator 20 has a rigid frame 22 to which two parallel linear bearings 24 are mounted. A floor covering specimen table 26 is mounted to a rotatable turntable 28 which is slidably mounted to the linear beatings 24. A rigid arm 30 is fixed to the frame 22. A pneumatic impactor 32 is mounted to the arm 30. A caster wheel 31 is also mounted to the arm 30 for rolling contact with the floor covering. The impactor 32 includes a pneumatic cylinder 34 with an extensible piston 36 to which a cylindrical heel 38 is mounted. The heel may be fabricated in a variety of shapes, weights, and hardnesses, to best simulate the type of foot traffic expected on the floor covering under test.

The impactor cylinder 34 is mounted to the arm 30 for movement of the piston 36 at an acute angle with respect to a vertical axis. The angle is preferably between 15 and 20 degrees with respect to a vertical axis. This range is simulative of common striking angles for most walkers. An impact angle of 17 degrees may be selected as a mean within this range for normal gait. The cylinder 34 is operated by an automatic controller 40 which is preferably an electronic computer, but which may alternatively be a system of mechanical cams or analog relays.

The cylinder 34 is mounted to the ann 30 such that the heel 38 will repetitively strike a floor covering 42 which is mounted to the specimen table 26. The speed of the impacts should be selected to simulate the actual rate of impact of a walker, for example 120 paces per minute. The force of the pneumatic cylinder 34 should be selected to represent the weight of a walker, for example 150 pounds. It should be noted that the rate and force of the impacts may be adjusted for floor coverings in specialized wear circumstances, i.e.: day care centers, schools, hospitals, retirement homes.

The specimen table 26 is mounted to the turntable 28 for rotatable motion beneath the impactor 32. The turntable is rotated by an electric motor to provide a means for rotating the impactor cylinder about a vertical axis with respect to the test specimen. Rotational motion alone, however, is not sufficient to achieve a wear pattern which is appropriately simulative of actual day-to-day foot traffic. The turntable 28 is thus mounted on a subframe 44 which is in turn mounted for back and forth motion on the linear bearings 24. A threaded rod or screw 46 is rotatably mounted to the frame 22 parallel to the linear bearings 24. The screw 46 is driven by a motor (not shown) under the control of the controller 40. The screw engages with a fitting 48 on the turntable subframe 44 in a conventional ball and screw arrangement to drive the turntable 28 and the specimen table 26 in a stable non-tilting manner on the linear beatings 24. The linear bearing arrangement and motor provide a means for displacing the specimen in a horizontal plane.

The specimen table 26 holds a floor covering specimen 42 so it may be subjected to the impactor 32 and allows readings to be taken on the condition of the specimen throughout the course of a test run.

Figure 2:
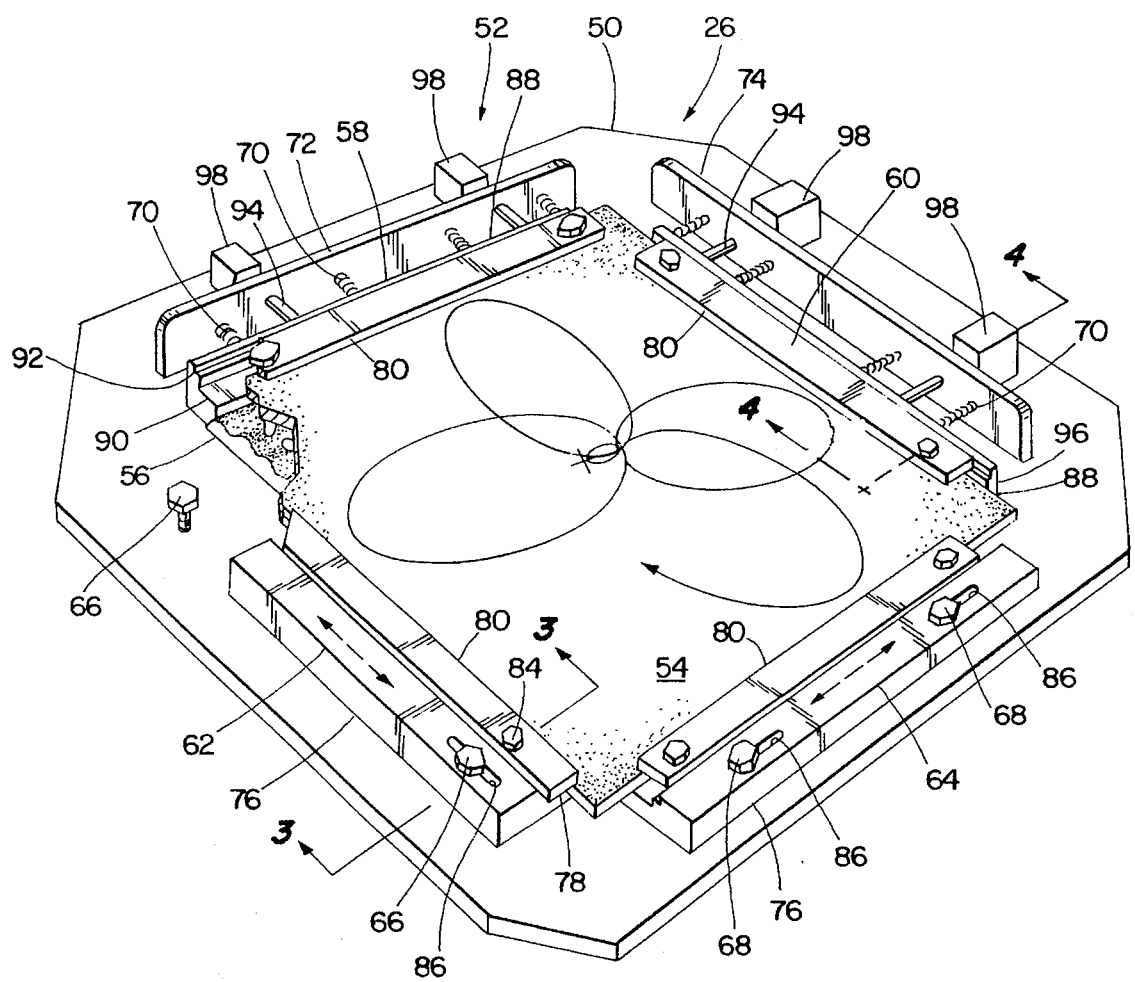
FIG. 2 is an isometric view, partially broken away, of the specimen table of the floor covering tester of FIG. 1.

As best shown in FIG. 2, the specimen table 26 has a rigid planar base 50, which is preferably a steel plate removably mounted to the turntable 28. The specimen table 26 is preferably removable to permit rapid exchange of one specimen for another on the simulator 20 to reduce machine down time.

The specimen table 26 has a bi-directional clamp assembly 52 which connects the top layer of the floor covering, for example a two foot by two foot square of carpet 54, to the base 50 over a substrate or backing 56, for example a rubber cushion or carpet pad. The bi-directional clamp assembly 52 allows the dimensional stability of the floor covering to be measured over the course of the test run. Carpet is nearly universally installed over a flexible backing. The backing provides resiliency which, if selected at appropriate levels, may reduce fatigue and prevent slippage of those who walk on the carpet. Typically, carpet is stretched to the walls of the room and then tacked or nailed along the carpet edges. Installed carpet overlies but is not connected to the backing material.

To properly simulate actual carpet installations, the specimen table 26 clamps the carpet 54 but does not clamp the backing 56. The bi-directional clamp assembly 52 is comprised of four clamps 58, 60, 62, 64. Each clamp grasps one edge of the carpet 54. Two clamps 62, 64, grasp adjacent edges of the carpet 54 and are pinned to the base 50 by bolts 66, 68. Two clamps 58, 60 grasp the edges opposite the clamps 62, 64 and are connected by tensioning springs 70 to two upright flanges 72, 74.

The pin mounted clamps 62, 64 have a generally L-shaped sliding member 76, best shown in FIG. 3, which rests on the table base 50. The sliding member has a ledge 78 which is approximately the height of the backing 56. A cover plate 80 is spaced above the ledge 78 and is positioned with one edge supported on a lip 82 of the sliding member. Clamping bolts 84 extend through holes in the cover plate 80 and threadedly engage with the ledge 78. The edge of the carpet is positioned between the cover plate 80 and the ledge 78 and is clamped therebetween by tightening the bolts 84.

Each sliding member 76 has at least two slots 86 through which the bolts 66, 68 extend. The bolts 66, 68 do not clamp the sliding members 76 to the base 50. The sliding members 76 are tree to slide on the bolts 66, 68 but only along a single axis. Thus the spring connected clamps 58, 60 may be displaced away from the pin-connected clamps 62,64, but the edges of the carpet 54 will always remain perpendicular to one another.

Each spring-connected clamp 58, 60, has a sliding member 88 which is generally L-shaped as best shown in FIG. 4. Each sliding member 88 rests on the table base 50 and has a ledge 90 which is approximately the height of the backing 56. A cover plate 80 is spaced above the ledge 90 and is positioned with one edge supported on a lip 92 of the sliding member. Clamping bolts 84 extend through holes in the cover plate 80 and threadedly engage with the ledge 90. The edge of the carpet is positioned between the cover plate 80 and the ledge 90 and is clamped therebetween by tightening the bolts 84.

The springs 70 extend between the flanges 72, 74 and the sliding members 88. The springs 70 exert a substantially constant force on the carpet and retain it under constant tension. Appropriate spring tensions would be in the range of 10 to 30 pounds. As the two perpendicular spring-connected sliding members 88 are independent of one another, it is possible to apply different spring tension to each direction of carpet stretch.

Measuring holes 94 are located in the flanges 72, 74 which permit the gauging of the carpet extension as the test progresses. By monitoring the distance between a point on a fixed flange 72, 74 and a point on the movable sliding member 88, it is possible to accurately determine the amount of carpet stretch at any time. These measurements may be taken by inserting a micrometer or scale rod through the hole 94 into contact with the vertical exterior face 96 of the sliding member 88. Alternatively, extensometers 98 may be mounted to the table base 50, as best shown in FIG. 4. Each extensometer 98 has a shaft 100 which engages with the vertical face of the 96 of the sliding member 88. The extensometer 98 produces an electrical signal proportional to the extension of the shaft 100 which is transmitted to the controller 40 or a separate chart recorder for future analysis.

The extensometers 98 may be a conventional linear variable differential transformer (LVDT). LVDT's are accurate and easily interfaced to a computer controller. A LVDT consists of a set of three coaxial wire coils all potted into a cylindrical unit with an opening through the coil axes. Into this opening a loose fitting metal plug is inserted. The coil is attached to the specimen table base 50 and the plug is connected to the sliding member of an edge clamp 88. Relative motions of the carpet 54 with respect to its support plate 50 causes corresponding relative motions of the metal plug along the axis of the coil assembly. The coils are connected as part of an electrical circuit and act like a transformer with primary and secondary windings. A constant excitation of the primary winding is translated into variable excitation of the secondary windings as the plug moves inside the coils. This variable signal is processed and becomes a measure of the relative motion between the floor covering specimen 42 and the specimen table 26. An electronic circuit translates the measurement into computer readable signals. The controller preferably provides a means for storing the displacement data detected by the extensometers, for example in RAM or on magnetic medium for future analysis and printout. An alternative means for storing the data would be in graphic form through a chart recorder connected to receive electrical signals from the extensometers.

The specimen table 26 thus allows a particular carpet to be tested with a variety of cushion or backing materials, to assist in determining which floor covering system will be most appropriate for a particular application.

The simulator 20 may be employed to test the performance of a floor covering system under a range of wear conditions. Although vinyl flooring, wood flooring, marble or terrazzo flooring are usually unilayer floor coverings, cabinet is commonly installed as part of a floor covering system which comprises a carpet layer stretched in place over a resilient cushion. Carpet is produced from a wide variety of materials in a multitude of weaves and styles. Numerous cushions are also available. Although generalizations about particular carpets and cushions may be made, there is no strictly analytical method of predicting the performance of a particular carpet with a particular cushion. The myriad possibilities of combinations and the unpredictable long term results of any selected combination, require a straight forward and effective testing regimen which will uniformly compare the performance of one floor covering system with another.

By utilizing the apparatus 20, manufacturers, insurers, maintenance providers, and environmental regulators may assess the performance of floor covering systems and relate that performance to their needs.

To generate a test of a floor covering system, the cushion 56 is cut to a size smaller than the carpet specimen 54, and is positioned directly on the specimen table base plate 50 within the bi-directional clamping assembly 52, but not in engagement with the clamping assembly. The cushion 56, thus freely positioned, simulates the installation characteristics of an actual environment, in which the underlaying cushion is not stretched. The carpet specimen 54 is next positioned over the cushion 56 so that the edges of the specimen overlie the ledges 78, 90 of the clamping assembly sliding members 76, 88. The cover plates 80 are then positioned over the specimen 54 and the bolts 84 are tightened to clamp the specimen to the clamps 58, 60, 62, 64.

Once clamped in place the carpet 54 is tensioned to the desired levels by adjusting the springs 70. As some carpets have different properties in the lateral and longitudinal directions, it may in some cases be desirable to apply a different tension to the warp of the carpet then to the weft. The spring tensions will preferably be set to mimic the installation specifications for the floor covering system under analysis.

It should be noted that, for minimum down-time on the simulator 20, floor covering systems may be mounted to multiple specimen tables 26 for rapid insertion and removal from the frame 22.

After the floor covering system has been installed on the specimen table 26 beneath the impactor 32, the angle of attack of the cylinder 34 is set as desired, usually at an angle of 15–20 degrees. The controller 40 is then activated to begin the reciprocal motion of the cylinder piston 36 and the attached heel 38. If desired, the caster wheel 31 may be attached to simulate wheeled chair or cart traffic at the same time.

The turntable 28 rotates beneath the reciprocating heel 38 to simulate a constantly changing angle of attack with respect to the carpet. The screw 46 is also rotated by an electric motor to drive the subframe 44 on the linear bearings 24 to reciprocate in a horizontal plane the rotating specimen table 26. The screw 46 is driven in one direction until the table reaches the end of its travel and then is momentarily halted, while the electric motor changes direction, and is then driven in the reverse direction to cause the specimen table 26 to travel to the opposite end of the linear bearings 24.

Figure 8:
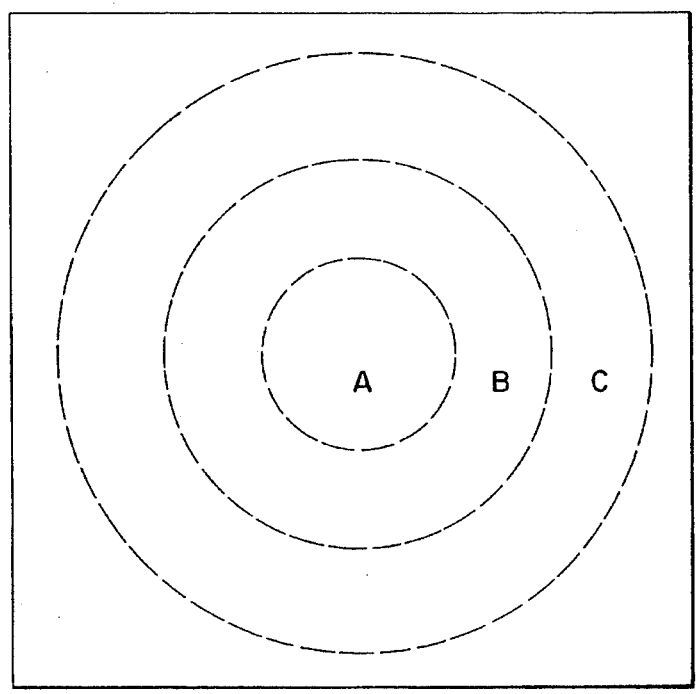
FIG. 8 is a graph indicating regions of impact frequency in a floor covering sample worked in the apparatus of FIG. 1.
Figure 9:
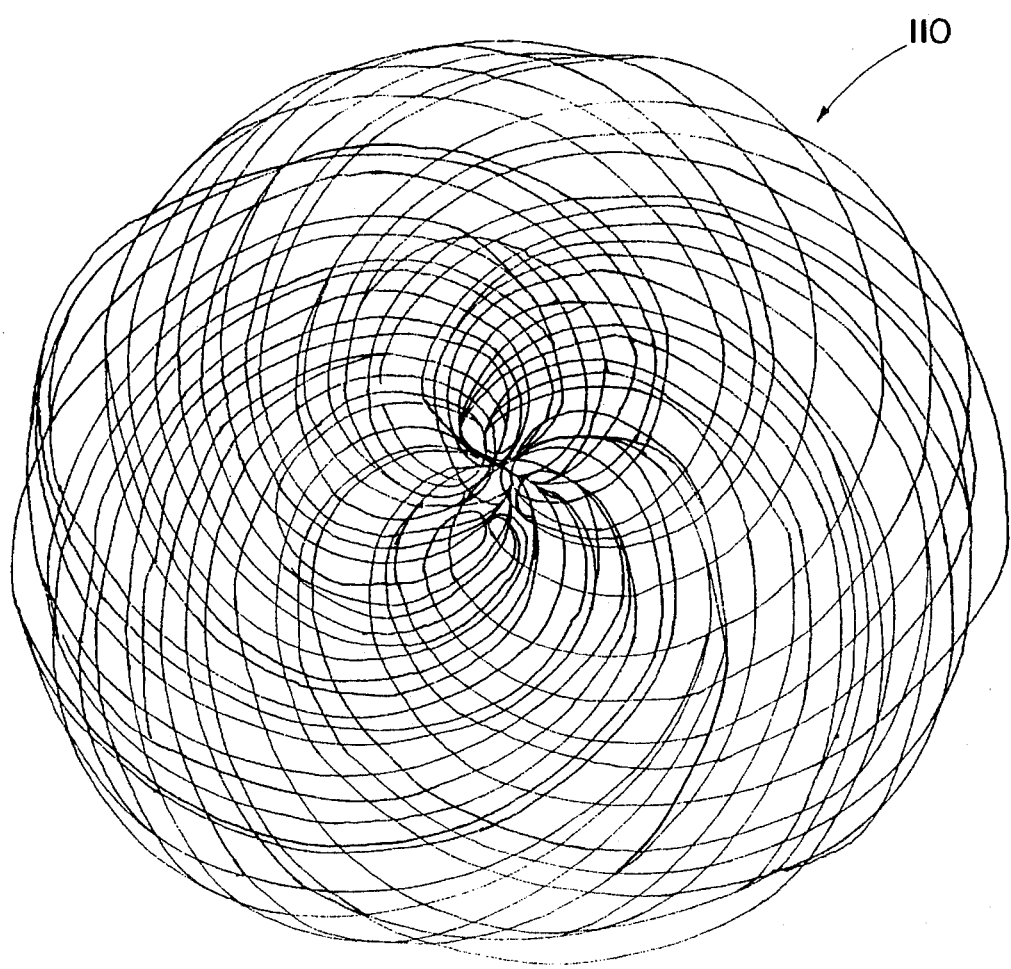
FIG. 9 is a schematic view of the path traced by the impactor of the apparatus of FIG. 1 over an extending testing period.

This compound motion of subframe 44 and turntable 28 produces a pattern 110 of impacts shown in FIG. 9. This pattern 110 is particularly effective in generating a useful test specimen in that the impacts are delivered over a range of angles of attack, i.e.: the angle of impact with respect to the two-dimensional plane of the carpet, and are clustered in linearly decreasing number. As shown in FIG. 8, a tested specimen may be divided into annular or circular regions A, B, C of decreasing numbers of impacts. For example, the inner region A which represents three inch radius from dead center of a two by two foot specimen would include 48.3 percent of the impacts, region B representing an annulus three to six inches from the center would include 16.7 percent of total impacts, and region B which is an annulus of six to nine inches, would include 9.3 percent of the impacts. Thus a single test specimen acts as its own control, having portions which are entirely unworked, portions which are heavily worked, and portions representing a range of wear in between the two extremes.

There is a straight linear decline in number of impacts from the center out to the radial edge. An analyst may take measures of pile thickness and determine how pile thickness degrades with increased working on a single worked test specimen. On a very stable material, it is possible to measure change of 5 thousandths of an inch.

Figure 7:
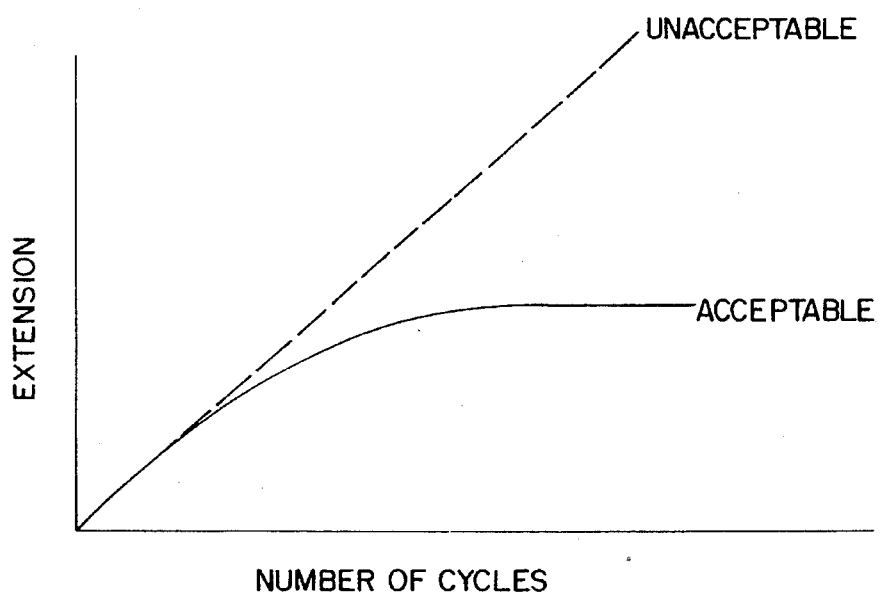
FIG. 7 is a graph showing carpet extension versus number of impact cycles for two carpet types as determined by the apparatus of FIG. 1.

The extensometers 98 provide data during the course of the test concerning the degree to which the carpet specimen is stretching or creeping. Although dimensional stability over time is important, it is particularly valuable to be able to correlate number of impacts with stretch. As shown in the chart of FIG. 7, a carpet which stretches under initial working, but which over time assumes stable dimensions is acceptable. However, a carpet which continues to stretch as impacts increase will generally be unacceptable.

It should be noted that in an apparatus lacking extensometers, the stretch data may be taken manually by intermittently interrupting the test to take measurements of the degree of carpet stretch.

It should be noted that the apparatus 20 may be utilized to prepare floor coverings other than carpet for analysis. For example, vinyl or tile floor coverings may be cycled through the test and subjected to multiple impacts by the simulated heel to detect degradation in surface finish and performance. Different surface treatments and finishes may thus be compared to determine which best suits a planned use. For example, the durability of slip resistant finishes may be tested. In addition to testing stretch performance of resilient floor coverings, the apparatus 20 conditions material for further examination and inspection. Post test examinations may include tests of tuft bind, lamination strength, compression set, tip flare, pile reversal, and pile thickness. Again, the linear decrease in amount of working provides a temporal representation of carpet wear which corresponds either to increased time or traffic.

Another application of the advantageous simulative properties of the apparatus 20 is in soil conditioning tests of carpets and other floor coverings. To simulate the effect of soiling on a floor covering over an extended period of foot traffic, the floor covering is placed on the simulator 20 as described above. If desired, a mask formed of a sheet of masonite or corrugated paper board with a central hole removed may be placed over the sample to preserve a control area which remains unsoiled. Fine grain soil which has been carefully weighed is dispersed over the floor covering as the impactor is cycled and moved with respect to the floor covering. At spaced intervals the floor covering may be subjected to vacuuming. At the conclusion of the test, soil will be worked into the floor covering to different degrees, depending on the distance from the specimen center. The sample may then be subjected to careful analysis to determine performance.

The tested sample evidences any textural distortion of the carpet surface. Textural distortion, such as pile shading, and reverse pile, is the form of floor covering degradation which is most readily perceptible to a carpet consumer because it contributes to the poor the appearance of the carpet. The samples produced by the simulator 20 provide a range of textural distortion regions for analysis by a manufacturer or floor covering consumer, to aid in redesigning the carpet or choosing an alternative material.

An alternative means for maintaining tension on the floor covering specimen 42 within the specimen table 26 is shown in FIG. 6. In place of springs 70, a double acting pneumatic cylinder 112 is mounted to the table base 50 to extend between the base and the sliding member 88. The cylinder 112 is under the control of the controller 40 and may be operated to supply a constant tension to the carpet, or to maintain a constant extension of the carpet, or to supply some variable tension which is deemed to best simulate the actual conditions of carpet use. The cylinder 112 is preferably pin-connected for pivotal motion about vertical axes to the base 50 and to the slider member 88.

Figure 10:
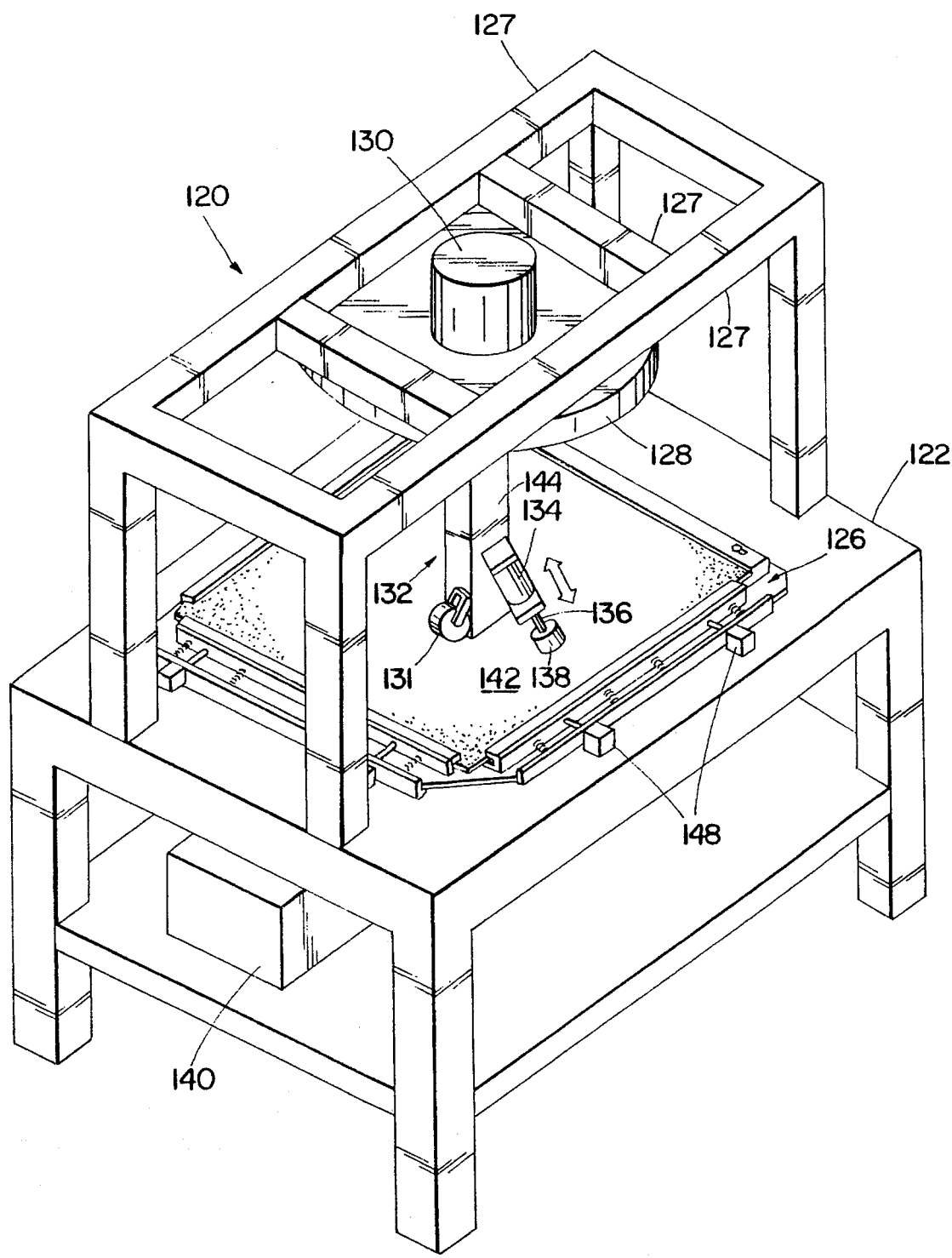
FIG. 10 is an isometric view of an alternative embodiment floor covering tester of the present invention.

An alternative embodiment floor covering foot force impact simulator 120 is shown in FIG. 10. The simulator 120 has a frame 122 with a specimen table 126 fixed in place. The fixed specimen table 126 facilitates instrumentation of the table and transmission of the data gathered to a computer controller 140. The frame 122 includes upper beams 127 which are spaced above the specimen table 126. A turntable 128 is fixed to the underside of the upper beams 127. A rotating pneumatic union 130 extends through the turntable 128 such that pneumatic conduits (not shown) may extend through the rotating turntable 128 and supply air pressure to the impactor assembly 132 and any other pneumatic accessories mounted on the underside of the turntable.

Figure 11:
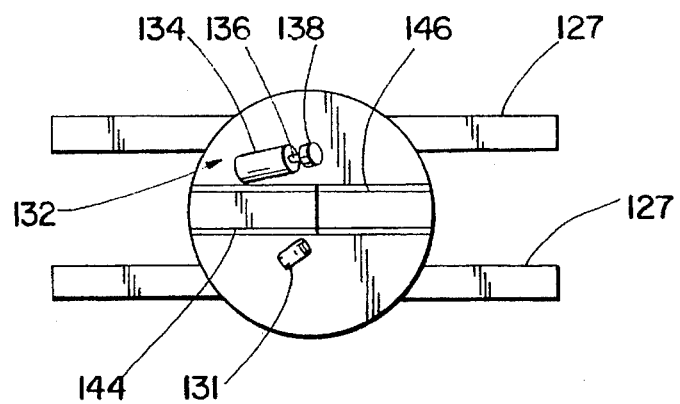
FIG. 11 is a bottom plan view of the turntable, carriage, and impactor assembly of the apparatus of FIG. 10.

The impactor assembly 132, as shown in FIG. 11, includes a pneumatic cylinder 134 with a rubber heel 138 mounted to a reciprocating piston 136. The cylinder 134 is mounted to a vertically extending carriage 144 which travels on a rectilinear track 146 which extends diametrically across the underside of the turntable 128. The track 146 may include pneumatic drive means such as a conventional rodless cylinder such as that manufactured by Miller Fluid Power of Bensenville, Ill., or, alternatively, it may incorporate a chain or screw drive. The cylinder 134 may be adjusted on the carriage 144 for a desired impact angle. A caster wheel 131 is removably connected to the carriage 144 to simulate chair traffic on the test specimen if desired.

The combination of the rotating motion of the turntable 128 and the linear motion of the impactor carriage 144 gives the simulator 120 the ability to produce the same relative motion between the reciprocating heel 138 and a floor covering specimen 142 as is produced by the simulator 20. The simulator 120 however, is capable of generating the desired pattern 110 of FIG. 9 without moving the specimen 142 at all.

The fixed specimen table 126 allows the extensometers 148 also to be fixed, and hence hardwired to the controller 140. Although vibrations at the time of impact of the impactor heel 138 may interfere with continuous readings from the extensometers 148, readings may be timed to coincide with the upward travel of the piston 136 to cyclicly detect the extension of the specimen 142 undergoing testing. The specimen table may, alternatively, be outfitted with the pneumatic controlled tensioning cylinders 112, shown in FIG. 6 and described more fully above.

Figure 12:
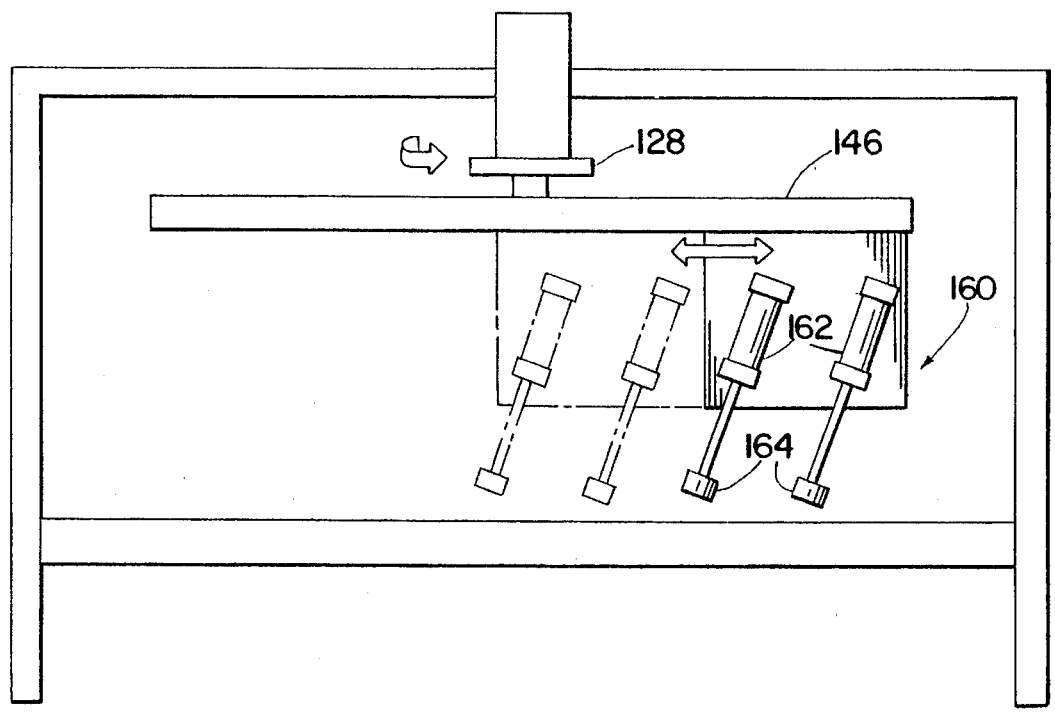
FIG. 12 is a schematic view of another alternative embodiment floor covering tester of the present invention.
Figure 13:
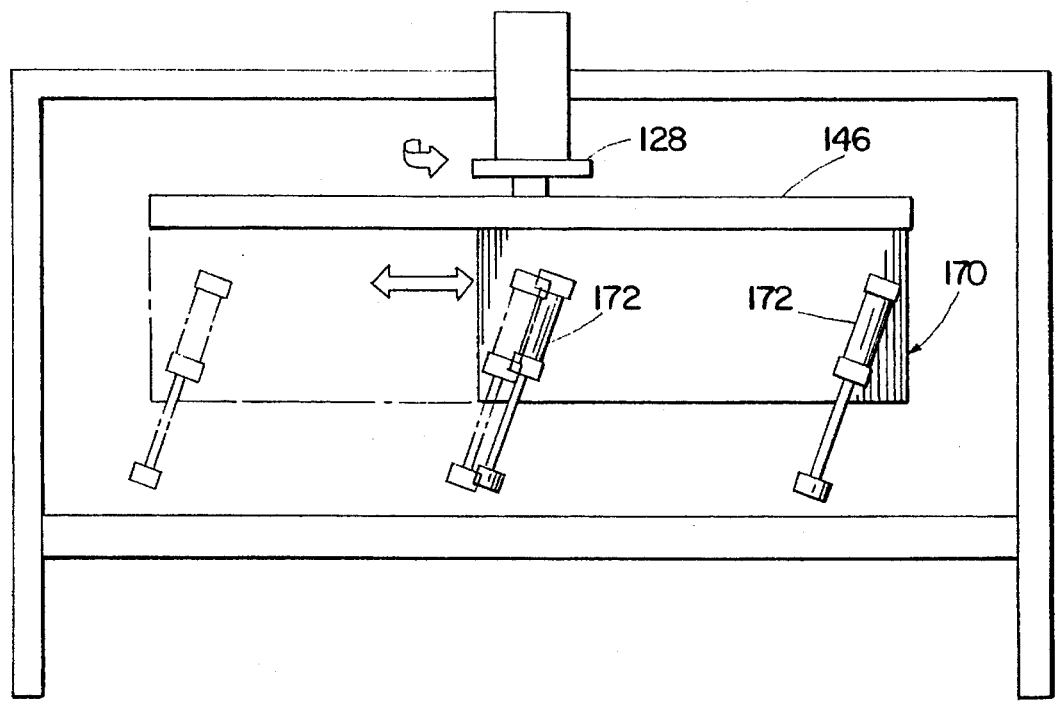
FIG. 13 is a schematic view of yet another floor covering tester of the present invention.

Alternative impactor assemblies for mounting on the simulator 120 are shown schematically in FIGS. 12 and 13. The carriage 160, shown in FIG. 12, has two impactor cylinders 162 each with an impacting heel 164. The carriage 160 is mounted for reciprocating linear motion on the track 146 from the center of the turntable 128 to the periphery. By utilizing two impactor cylinders, this apparatus may accumulate twice the number of impacts on a floor covering specimen in a given time period than a single cylinder apparatus.

The carriage 170, shown in FIG. 13, also has two impactor cylinders 172. The carriage 170 is somewhat greater then one half the diameter of the turntable 128, and reciprocates to alternatively bring one cylinder and than the other into position at the center of the turntable. Thus each cylinder traverses the radius of the turntable.

It is understood that the invention is not confined to the particular construction and arrangement of parts herein illustrated and described, but embraces such modified forms thereof as come within the scope of the following claims.

We claim:

1. A carpet wear testing apparatus, comprising:
   (a) a frame;
   (b) a table mounted on the frame;
   (c) a bidirectional tensioning clamp mounted to the table, the clamp providing adjustable tensioning force along two directions for holding a carpet test specimen in a selected state of planar tension adjacent a backing material that is not placed in tension;
   (d) at least one displacement detector mounted on the table and linked to the test specimen for detecting stretching in the test specimen;
   (d) an impactor mounted to the frame, the impactor having a reciprocating heel for repetitively engaging the test specimen; and
   (f) means for recording the stretching of the test specimen as detected by the displacement detector with respect to the number of repetitive engagements of the test specimen by the shoe.

2. The apparatus of claim 1 wherein the table is mounted to the frame for translational and rotational movement, and the backing material is retained adjacent the carpet test specimen by the table and at least one ledge.

3. The apparatus of claim 1 wherein the impactor comprises a pneumatic piston mounted to the frame and wherein the heel is mounted to the piston for repetitive reciprocation so as to bring the heel into contact with the test specimen.

4. The apparatus of claim 1 wherein a backing material comprising a carpet cushion underlies the carpet test specimen, and wherein the clamps support the carpet tensioned over the cushion.

5. A carpet wear testing apparatus, comprising:
   (a) a frame;
   (b) a table mounted on the frame;
   (c) a bi-directional tensioning clamp mounted to the table, the clamp providing adjustable tensioning force along two directions for holding a carpet test specimen in a selected state of planar tension;
   (d) at least one displacement detector mounted on the table and linked to the test specimen for detecting stretching in the test specimen;
   (d) an impactor mounted to the frame, the impactor having a reciprocating heel for repetitively engaging the test specimen;
   (f) means for recording the stretching of the test specimen as detected by the displacement detector with respect to the number of repetitive engagements of the test specimen by the shoe; and
   (g) a general purpose computer controlling the tension produced by the clamp and receiving the displacement measurements detected by the displacement detector, and wherein the impactor is adjustable in force and rate of reciprocation under control of the computer and wherein the computer records the stretching of the test specimen with respect to the number of repetitive engagements of the test specimen by the heel.

6. An apparatus for simulating foot traffic on a floor covering, comprising:
   (a) a frame;
   (b) a table mounted to the frame which supports a floor covering specimen in a state of tension for wear-testing adjacent an untensioned backing material;
   (c) a reciprocating cylinder mounted to the frame above the table, wherein the cylinder is mounted for travel at an acute angle with respect to a vertical axis to impact the specimen;
   (d) a heel mounted to the cylinder which repetitively impacts the specimen;
   (e) means for displacing in a horizontal plane the cylinder with respect to the specimen; and
   (f) means for rotating continuously the cylinder about a vertical axis to cause the heel to strike the specimen from a changing angle of attack in a horizontal plane as the cylinder is displaced in the horizontal plane to thereby simulate shear forces of a human footstep on the specimen.

7. The apparatus of claim 6 wherein the table is mounted to at least one linear bearing which is connected to the frame, and wherein the means for displacing the cylinder in a horizontal plane with respect to the specimen comprises a motor-driven ball and screw arrangement which engages with and moves the table.

8. The apparatus of claim 6 wherein the table is mounted to a rotatable turntable, and wherein the means for rotating the cylinder about a vertical axis comprises an motor which rotates the turntable.

9. An apparatus for simulating foot traffic on a floor covering, comprising:
   (a) a frame;
   (b) a table mounted to the frame which supports a floor covering specimen for wear-testing adjacent a backing material which is not held in a state of tension:
   (c) a reciprocating cylinder mounted to the frame above the table, wherein the cylinder is mounted for travel at an acute angle with respect to a vertical axis to impact the specimen, wherein the angle between the cylinder and the vertical axis is between 15 and 20 degrees;
   (d) a heel mounted to the cylinder which repetitively impacts the specimen;
   (e) means for displacing a horizontal plane the cylinder with respect to the specimen;
   (f) means for rotating the cylinder about a vertical axis to cause the heel to strike the specimen from a changing angle of attack in a horizontal plane as the cylinder is displaced in the horizontal plane to thereby simulate shear forces of a human footstep on the specimen.

10. An apparatus for testing a floor covering system comprising:
    (a) a frame;
    (b) a table connected to the frame which supports a cushion;
    (c) a clamp assembly connected to the table, the assembly having at least four clamping members slidably engaged with the table outwardly of the cushion, and each clamping member has a ledge which is elevated above the surface of the table such that a carpet specimen may overlie the ledges and the cushion and be clamped to and tensioned by the clamping members without clamping or tensioning the cushion; and (d) a heel movably mounted to the frame for reciprocating impacting motion of the combined carpet and cushion assembly, wherein the impacting of the heel on the carpet and cushion assembly simulates human footsteps.

11. The apparatus of claim 10 further comprising:

a) a rotating turntable to which the table is connected;

b) at least one linear bearing to which the turntable is connected for motion in a horizontal plane; and c) an arm which extends from the frame to a position above the table, wherein the heel is mounted to a reciprocating cylinder connected to the arm, and wherein the turntable rotates beneath the heel while the turntable is advanced on the linear bearing to impart a compound motion to the combined carpet and cushion assembly.

12. A method of testing carpet wear comprising the steps of:

(a) mounting a carpet test specimen having dimensions of length and width in a clamp which applies tension to the specimen in a plane defined by the test specimen while supporting an untensioned backing material adjacent the specimen;

(b) repetitively engaging the specimen with a heel mounted to an impactor;

(c) recording at selected time intervals the number of engagements of the shoe and at least one dimension of the test sample;

(d) plotting the number of impacts versus carpet extension in at least one dimension thus producing a means for determining whether the carpet test sample is dimensionally stable or unstable with greater and greater wear.

13. A method of testing carpet wear, further comprising the steps of:

(a) mounting a carpet test specimen having dimensions of length and width in a clamp which applies tension to the specimen in a plane defined by the test specimen;

(b) repetitively engaging the specimen with a heel mounted to an impactor;

(c) recording at selected time intervals the number of engagements of the shoe and the width and length of the test sample;

(d) plotting the number of impacts versus carpet extension in both width and length thus producing a means for determining whether the carpet test sample is dimensionally stable or unstable with greater and greater wear.

14. A method of testing carpet wear comprising the steps of:

(a) mounting a carpet test specimen having dimensions of length and width in a clamp which applies tension to the specimen in a plane defined by the test specimen;

(b) repetitively engaging the specimen with a heel mounted to an impactor;

(c) recording at selected time intervals the number of engagements of the shoe and at least one dimension of the test sample;

(d) plotting the number of impacts, wherein the number of impacts is a function of time, versus carpet extension in at least one dimension and wherein the plotting of time versus extension is used for determining whether the carpet test sample is dimensionally stable or unstable with greater and greater wear.

* * * * *